US009708631B2

(12) United States Patent
Higashide et al.

(10) Patent No.: US 9,708,631 B2
(45) Date of Patent: *Jul. 18, 2017

(54) MICROBIAL SYNTHESIS OF ALDEHYDES AND CORRESPONDING ALCOHOLS

(71) Applicant: Easel Biotechnologies, LLC, Culver City, CA (US)

(72) Inventors: Wendy M. Higashide, Los Angeles, CA (US); Kwang Myung Cho, Sungnam-Si (KR); Shahrooz Rabizadeh, Los Angeles, CA (US)

(73) Assignee: Easel Biotechnologies, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/857,592

(22) Filed: Sep. 17, 2015

(65) Prior Publication Data

US 2016/0130611 A1    May 12, 2016

Related U.S. Application Data

(62) Division of application No. 14/004,135, filed as application No. PCT/US2012/029013 on Mar. 14, 2012, now Pat. No. 9,206,443.

(Continued)

(51) Int. Cl.
   *C12P 7/02*    (2006.01)
   *C12P 7/16*    (2006.01)
   (Continued)

(52) U.S. Cl.
   CPC .............. *C12P 7/16* (2013.01); *C07C 29/141* (2013.01); *C12N 1/16* (2013.01); *C12N 1/20* (2013.01);
   (Continued)

(58) Field of Classification Search
   None
   See application file for complete search history.

(56) References Cited

U.S. PATENT DOCUMENTS

| 4,900,670 A | 2/1990 | Zall et al. |
| 7,326,551 B2 | 2/2008 | Maupin-Furlow et al. |

(Continued)

FOREIGN PATENT DOCUMENTS

| WO | 94-06924 A1 | 3/1994 |
| WO | 2009-086423 A2 | 7/2009 |

(Continued)

OTHER PUBLICATIONS

Atsumi, S. et al., "Engineering the isobutanol biosynthetic pathway in *Escherichia coli* by comparison of three aldehyde reductase/alcohol dehydrogenase genes," Appl. Microbiol. Biotechnol. (2010) 85: 651-657.

(Continued)

*Primary Examiner* — Robert Mondesi
*Assistant Examiner* — Richard Ekstrom
(74) *Attorney, Agent, or Firm* — Fish & Tsang, LLP (57) ABSTRACT

An improved process for alcohol production includes microbial fermentation using a genetically modified microorganism to produce substantial quantities of aldehydes that are stripped from the fermentation medium and condensed. So produced aldehydes are converted in an ex vivo process to corresponding alcohols.

25 Claims, 1 Drawing Sheet

Related U.S. Application Data (60) Provisional application No. 61/452,519, filed on Mar. 14, 2011.

(51) Int. Cl.

| | | |
|---|---|---|
| *C12N 1/20* | (2006.01) | |
| *C12N 1/16* | (2006.01) | |
| *C12N 9/88* | (2006.01) | |
| *C12N 15/63* | (2006.01) | |
| *C12N 15/67* | (2006.01) | |
| *C12P 7/24* | (2006.01) | |
| *C12N 9/04* | (2006.01) | |
| *C12N 9/10* | (2006.01) | |
| *C12N 15/52* | (2006.01) | |
| *C07C 29/141* | (2006.01) | |
| *C12N 15/70* | (2006.01) | |
| *C12N 15/74* | (2006.01) | |

(52) U.S. Cl.
CPC ......... *C12N 9/0006* (2013.01); *C12N 9/1022* (2013.01); *C12N 9/88* (2013.01); *C12N 15/52* (2013.01); *C12N 15/63* (2013.01); *C12N 15/67* (2013.01); *C12N 15/70* (2013.01); *C12N 15/74* (2013.01); *C12P 7/02* (2013.01); *C12P 7/24* (2013.01); *Y02E 50/17* (2013.01)

(56) References Cited

U.S. PATENT DOCUMENTS

| | | | |
|---|---|---|---|
| 7,851,188 | B2 | 12/2010 | Donaldson et al. |
| 7,993,889 | B1 | 8/2011 | Donaldson et al. |
| 8,048,666 | B1 | 11/2011 | Green et al. |
| 8,097,439 | B2 | 1/2012 | Alibhai et al. |
| 8,692,024 | B2 | 4/2014 | Kouba et al. |
| 9,206,443 | B2 * | 12/2015 | Higashide ................ C12N 9/88 |
| 2009/0081746 | A1 | 3/2009 | Liao et al. |
| 2009/0246841 | A1 | 10/2009 | Jamieson et al. |
| 2010/0003739 | A1 | 1/2010 | Duhring et al. |
| 2010/0062505 | A1 | 3/2010 | Gunawardena et al. |
| 2010/0209986 | A1 | 8/2010 | Liao et al. |
| 2010/0255552 | A1 | 10/2010 | Doyle et al. |
| 2011/0008861 | A1 | 1/2011 | Berry et al. |
| 2011/0020889 | A1 | 1/2011 | Feldman et al. |
| 2011/0183392 | A1 | 7/2011 | Feldman et al. |
| 2011/0201083 | A1 | 8/2011 | Liao et al. |
| 2011/0250660 | A1 | 10/2011 | Liao et al. |
| 2012/0028323 | A1 | 2/2012 | Feldman et al. |
| 2012/0034665 | A1 | 2/2012 | Haas et al. |
| 2012/0045809 | A1 | 2/2012 | Buelter et al. |
| 2012/0209021 | A1 | 8/2012 | Kouba et al. |
| 2014/0322774 | A1 | 10/2014 | Cho et al. |

FOREIGN PATENT DOCUMENTS

| | | |
|---|---|---|
| WO | 2009-149240 A1 | 12/2009 |
| WO | 2010-062597 A1 | 6/2010 |
| WO | 2010-075504 A2 | 7/2010 |
| WO | 2011-005554 A2 | 1/2011 |
| WO | 2011-057288 A2 | 5/2011 |
| WO | 2011-128907 A1 | 10/2011 |
| WO | 2011-140516 A2 | 11/2011 |
| WO | 2011-159894 A1 | 12/2011 |

OTHER PUBLICATIONS

Atsumi, S., et al., "Non-fermentative pathways for synthesis of branched-chain higher alcohols as biofuels," Nature, vol. 451 (3); Jan. 2008; pp. 86-90.

Zhang, K., et al., "Expanding metabolism for biosynthesis of nonnatural alcohols," PNAS (Proceedings of the National Academy of Science) vol. 105 (52); Dec. 30, 2008, pp. 20653-20658.

ISA/KR, International Search Report and Written Opinion for Application No. PCT/US2012/029013, Sep. 27, 2012, 11 pgs.

Baez, A., et al., "High-flux isobutanol production using engineered *Escherichia coli*: a bioreactor study with in situ product removal," Appl Microbial Biotechnol vol. 90, pp. 1681-1690 (2011).

Atsumi, S., et al., "Direct photosynthetic recycling of carbon dioxide to isobutyraldehyde," Nature Biotechnology, vol. 7, No. 12, Dec. 2009, pp. 1177-1182.

Cann, A.F., et al., "Production of 2-methyl-1-butanol in engineered *Escherichia coli*," Appl Micro Biol Biotechnol (2008) 81:89-98.

Wecker et al., "Production of acetaldehyde by Zymomonas mobilis", Applied and Environmental Microbiology, vol. 53, No. 12, pp. 2815-2820, 1987.

Simmonds et al., "Formation of benzaldehyde by Pseudomonas putida ATCC 12633", Applied Microbiology and Biotechnology, vol. 50, pp. 353-358, 1998.

* cited by examiner

SEQUENCE LISTING

<160> NUMBER OF SEQ ID NOS: 12

<210> SEQ ID NO 1
<211> LENGTH: 21
<212> TYPE: DNA
<213> ORGANISM: Artificial

```
<220> FEATURE:
<223> OTHER INFORMATION: synthetic oligonucleotide

<400> SEQUENCE: 1
acgcgtgcta gaggcatcaa a                                              21

<210> SEQ ID NO 2
<211> LENGTH: 37
<212> TYPE: DNA
<213> ORGANISM: Artificial
<220> FEATURE:
<223> OTHER INFORMATION: synthetic oligonucleotide

<400> SEQUENCE: 2
tgtacctttc tcctctttaa tgaattcggt cagtgcg                             37

<210> SEQ ID NO 3
<211> LENGTH: 48
<212> TYPE: DNA
<213> ORGANISM: Artificial
<220> FEATURE:
<223> OTHER INFORMATION: synthetic oligonucleotide

<400> SEQUENCE: 3
ttaaagagga gaaggtaca atgttgacaa aagcaacaaa agaacaaa                  48

<210> SEQ ID NO 4
<211> LENGTH: 40
<212> TYPE: DNA
<213> ORGANISM: Artificial
<220> FEATURE:
<223> OTHER INFORMATION: synthetic oligonucleotide

<400> SEQUENCE: 4
catggtgatt cctcgtcgac ctagagagct ttcgttttca                          40

<210> SEQ ID NO 5
<211> LENGTH: 37
<212> TYPE: DNA
<213> ORGANISM: Artificial
<220> FEATURE:
<223> OTHER INFORMATION: synthetic oligonucleotide

<400> SEQUENCE: 5
gtcgacgagg aatcaccatg gctaactact tcaatac                             37

<210> SEQ ID NO 6
<211> LENGTH: 40
<212> TYPE: DNA
<213> ORGANISM: Artificial
<220> FEATURE:
<223> OTHER INFORMATION: synthetic oligonucleotide

<400> SEQUENCE: 6
atggtatatc tccttccggg ttaacccgca acagcaatac                          40

<210> SEQ ID NO 7
<211> LENGTH: 38
<212> TYPE: DNA
<213> ORGANISM: Artificial
<220> FEATURE:
<223> OTHER INFORMATION: synthetic oligonucerlotide

<400> SEQUENCE: 7
cccggaagga gatataccat gcctaagtac cgttccgc                            38
```

-continued

```
<210> SEQ ID NO 8
<211> LENGTH: 40
<212> TYPE: DNA
<213> ORGANISM: Artificial
<220> FEATURE:
<223> OTHER INFORMATION: synthetic oligonucleotide

<400> SEQUENCE: 8
ttgatgcctc tagcacgcgt ttaacccccc agtttcgatt                              40

<210> SEQ ID NO 9
<211> LENGTH: 27
<212> TYPE: DNA
<213> ORGANISM: Artificial
<220> FEATURE:
<223> OTHER INFORMATION: synthetic oligonucleotide

<400> SEQUENCE: 9
tctagaggca tcaaataaaa cgaaagg                                            27

<210> SEQ ID NO 10
<211> LENGTH: 27
<212> TYPE: DNA
<213> ORGANISM: Artificial
<220> FEATURE:
<223> OTHER INFORMATION: synthetic oligonucleotide

<400> SEQUENCE: 10
ggtacctttc tcctctttaa tgaattc                                            27

<210> SEQ ID NO 11
<211> LENGTH: 40
<212> TYPE: DNA
<213> ORGANISM: Artificial
<220> FEATURE:
<223> OTHER INFORMATION: sythetic oligonucleotide

<400> SEQUENCE: 11
ttaaagagga gaaaggtacc atgtatacag taggagatta                              40

<210> SEQ ID NO 12
<211> LENGTH: 40
<212> TYPE: DNA
<213> ORGANISM: Artificial
<220> FEATURE:
<223> OTHER INFORMATION: synthetic oligonucleotide

<400> SEQUENCE: 12
ttttatttga tgcctctaga atgatttatt ttgttcagca                              40
```

MICROBIAL SYNTHESIS OF ALDEHYDES AND CORRESPONDING ALCOHOLS

This application is a divisional of U.S. application Ser. No. 14/004,135, filed Sep. 9, 2013, which is a national phase application of PCT/US2012/029013, filed Mar. 14, 2012, which claims priority to U.S. provisional application Ser. No. 61/452,519, filed Mar. 14, 2011.

The field of the invention is metabolic engineering of microorganisms to produce one or more chemicals, and especially aldehydes, that are then isolated and converted ex vivo to the corresponding alcohols.

BACKGROUND OF THE INVENTION

World production and consumption of aldehydes and other oxo-chemicals was nearly 9.6 million metric tons in 2005. Global capacity utilization increased to 84% in 2005 from 79% in 2001 as a result of stronger demand, increased production and rationalized capacity. Between 2001 and 2005, world capacity for aldehydes and other oxo-chemicals grew at an average annual rate of 1.6%, a lower rate than world consumption, which grew at an average annual rate of 3.4% during the same period.

Most commonly, aldehydes and other oxo-chemicals are currently being produced by refinery methods using petrochemicals derived from crude oil cracking. For example, C3 to C15 aldehydes are generated via hydroformylation of olefins with synthesis gas, and the so produced aldehydes are then converted to corresponding alcohols, acids, or other derivatives. Currently, the oxo-chemical in highest demand is n-butyraldehyde, followed by C6-C13 aldehydes for plasticizer alcohols, and isobutyraldehyde and C12-C18 aldehydes for detergent alcohols.

Microbial synthesis of biofuels using metabolically engineered microbial cells, and especially production of C2-C6 alcohols is well known in the art. For example, microbial ethanol production from carbohydrates is described in WO 94/06924 and ethanol production from $CO_2$ is reported in U.S. Pat. No. 8,048,666. Short-chain alcohol production from 2-keto acids using metabolically engineered cells is described in U.S. Pat. App. No. 2009/0081746, and numerous publications are directed to isobutanol production from metabolically engineered cells (e.g., U.S. Pat. Nos. 7,851,188 and 7,993,889, and in WO 2009/086423, WO 2009/149240, WO 2010/062597, and WO 2010/075504), and alcohol production from $CO_2$ using photosynthetically active organisms is described in US2011/0250660. Similar methods were also described by Kechun Zhang et al. in Proc. Nat. Acad. Sci. (2008), 105, no. 52: 20653-20658. C5-8 alcohol production from 2-keto acids using metabolically engineered cells was described in U.S. Pat. App. No. 2011/0201083, and production of fatty aldehydes from various carbon sources was reported in U.S. Pat. No. 8,097,439. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unfortunately, yield of alcohol using many of such processes is still relatively low. To improve yield of at least certain alcohols, endogenous alcohol dehydrogenases can be deleted or suppressed, and can be replaced with a recombinant dehydrogenase as described in WO 2009/149240A1. While such modifications are often desirable to at least some extent, other problems arise. For example, various alcohols are toxic to the cells producing the alcohol above a threshold concentration, which tends to limit the overall yield. Moreover, most microbially synthesized alcohols are completely miscible with the fermentation medium and need a rather energy consuming process for isolation. Worse, yet, some of the alcohols for azeotropic mixtures and are even more difficult to separate from the medium.

Thus, even though numerous systems and methods of production of aldehydes, oxo-chemicals, and corresponding alcohols are known in the art, several difficulties nevertheless remain. Therefore, there is still a need for improvement, particularly where such chemicals are produced using a microbial system.

SUMMARY OF THE INVENTION

The present invention is directed to devices and methods for production of aldehyde and alcohol compounds using a mixed synthetic process in which a metabolically engineered microbial cell uses a carbon source to produce an aldehyde that is then continuously or semi-continuously removed in the vapor phase from the fermentation medium. In particularly preferred aspects, the metabolically engineered microbial cell is substantially devoid of any alcohol production. The aldehyde is then condensed from the vapor phase and reduced ex vivo to the corresponding alcohol. Contemplated methods advantageously overcome various difficulties, especially various problems associated with product inhibition and separation of the alcohols from the fermentation medium.

In one aspect of the inventive subject matter a method of producing an alcohol includes a step of growing a plurality of microbial cells in a fermentation medium (preferably having glucose, fructose, sucrose, starch, cellulose, a hemicellulose, glycerol, carbon dioxide, a protein, a lipid, and/or an amino acid as carbon source), wherein the cells are genetically modified to have an increased metabolic activity as compared to non-genetically modified cells. It is especially preferred that the increased metabolic activity is an increased conversion of pyruvate or 2-ketobutyrate to an aldehyde, and a decreased alcohol dehydrogenase activity. Aldehyde produced by the cells is continuously or semi-continuously removed from the fermentation medium in the vapor phase. In another step, the aldehyde is condensed from the vapor phase, and in yet another step the condensed aldehyde is reduced to the corresponding alcohol.

While in some embodiments the increased metabolic activity is an increased conversion of pyruvate to acetaldehyde via a recombinant pyruvate decarboxylase, the increased metabolic activity in other embodiments is an increased conversion of 2-ketobutyrate to propanal via a recombinant 2-ketoisovalerate decarboxylase. Additionally, or alternatively, it is preferred that the microbial cells also have increased metabolic activity in decarboxylation of one or more of 2-ketovalerate, 2-ketocaproate, 2-ketoheptanoate, 2-ketooctanoate, 2-keto-3-methylvalerate, 2-keto-4-methylcaproate, 2-keto-5-methylheptanoate, 2-keto-6-methyloctanoate, 2-keto-isovalerate, 2-ketoisocaproate, 2-keto-5-methylhexanoate, or 2-keto-6-methylocatnoate via a recombinant 2-ketoisovalerate decarboxylase. Thus, especially preferred fermentation produces include acetaldehyde, propanal, butanal, and 2-methyl-1-propanal.

In still further contemplated aspects, the microbial cells have increased metabolic activity in branched carbon chain elongation of 2-ketobutyrate to 2-keto-3-methylvalerate via recombinant ilvGMCD genes or recombinant ilvBNCD genes, and/or increased metabolic activity in branched carbon chain elongation of pyruvate to 2-keto-isovalerate via recombinant alsS-ilvCD genes or recombinant ilvIHCD genes. It is still further particularly preferred that the microbial cells also have increased metabolic activity in linear carbon chain elongation via recombinant leuABCD genes.

While not limiting to the inventive subject matter, it is generally preferred that the decreased alcohol dehydrogenase activity in the microbial cells is decreased at least 70% and more typically at least 90% as compared to the non-genetically modified cells.

In particularly preferred methods, the step of removing the aldehyde in the vapor phase includes agitation of the fermentation medium, stripping the fermentation medium with an inert gas, stripping the fermentation medium with an oxygen containing gas, and/or temporarily binding the aldehyde to a binding agent. Most typically, the aldehyde is continuously removed from the fermentation medium. The so isolated aldehyde is then reduced to the corresponding alcohol, for example, using electrochemical reduction, enzymatic reduction, and/or a catalytic reduction with hydrogen.

Suitable microbial cells will be selected from the genera *Escherichia, Bacillus, Corynebacterium, Ralstonia, Zymomonas, Clostridium, Lactobacillus, Synechococcus, Synechocystis, Saccharomyces, Pichia, Candida, Hansenula*, and *Aspergillus*. Thus, particularly preferred microbial cells include *Escherichia coli, Bacillus subtilis, Synechococcus elongatus, Ralstonia eutropha*, and *Saccharomyces cerevisiae*.

Therefore, and viewed from a different perspective, a method of producing a metabolically engineered microbial cell for use in an production process in which a value product (e.g., alcohol) is ex vivo produced from an aldehyde will include a step of genetically modifying the microbial cells to have an increased conversion of pyruvate or 2-ketobutyrate to an aldehyde, and a further step of genetically modifying the microbial cells to have a decreased alcohol dehydrogenase activity such that the microbial cell is substantially devoid of alcohol production. In yet another step, the modified microbial cells are tested for generation in a fermentation medium of a volatile aldehyde in a quantity sufficient to allow stripping of the volatile aldehyde from the fermentation medium to thereby allow for an ex vivo conversion of the aldehyde to the value product (e.g., reduction of the aldehyde to a corresponding alcohol).

In especially preferred aspects, the microbial cell has increased metabolic activity in conversion of pyruvate to acetaldehyde via a recombinant pyruvate decarboxylase or an increased metabolic activity in conversion of 2-ketobutyrate to propanal via a recombinant 2-ketoisovalerate decarboxylase. Additionally, or alternatively, the microbial cell has an increased metabolic activity in linear carbon chain elongation via recombinant leuABCD genes, and/or an increased metabolic activity in branched carbon chain elongation of 2-ketobutyrate to 2-keto-3-methylvalerate via recombinant ilvGMCD genes or recombinant ilvBNCD genes or in branched carbon chain elongation of pyruvate to 2-keto-isovalerate via recombinant alsS-ilvCD genes or recombinant ilvIHCD genes.

Various objects, features, aspects and advantages of the inventive subject matter will become more apparent from the following detailed description of preferred embodiments, along with the accompanying drawing FIGURES in which like numerals represent like components.

DETAILED DESCRIPTION

The inventors have discovered that microbial cells can be metabolically engineered to substantially increase production of various (especially volatile) aldehydes that are not or only to a negligible degree further metabolized to the corresponding alcohols. Such approach is particularly unexpected as aldehydes are typically significantly more toxic than the corresponding alcohols, and as the aldehydes will be produced (and potentially accumulated in the cell) at an even faster rate due to the suppression of the endogenous alcohol dehydrogenases. The so produced aldehydes are then removed from the fermentation medium in the vapor phase, preferably by stripping the medium with a stripping gas in a continuous or semi-continuous manner (i.e., in an intermittent fashion throughout the fermentation process using at least two removal periods).

In especially preferred aspects of the inventive subject matter, the microbial cell is genetically modified to have an increased conversion of pyruvate or 2-ketobutyrate to an aldehyde, and a decreased alcohol dehydrogenase activity. Increased conversion of pyruvate or 2-ketobutyrate to the aldehyde is most typically due to the presence of one or more nucleic acid constructs (e.g., provided as plasmids and/or integrated into the host cell genome) that encode one or more genes that lead to the formation of enzymes that catalyze a reaction in the conversion of pyruvate or 2-ketobutyrate to the aldehyde. Thus, in most cases, the increased conversion is due to a higher throughput of metabolites through a sequence of biochemical reactions in the cell that lead to the desired aldehyde end product(s). Of course, it should be appreciated that one or more endogenous (non-recombinant) enzymes may be part of the sequence of biochemical reactions in the cell.

Figure 1A:
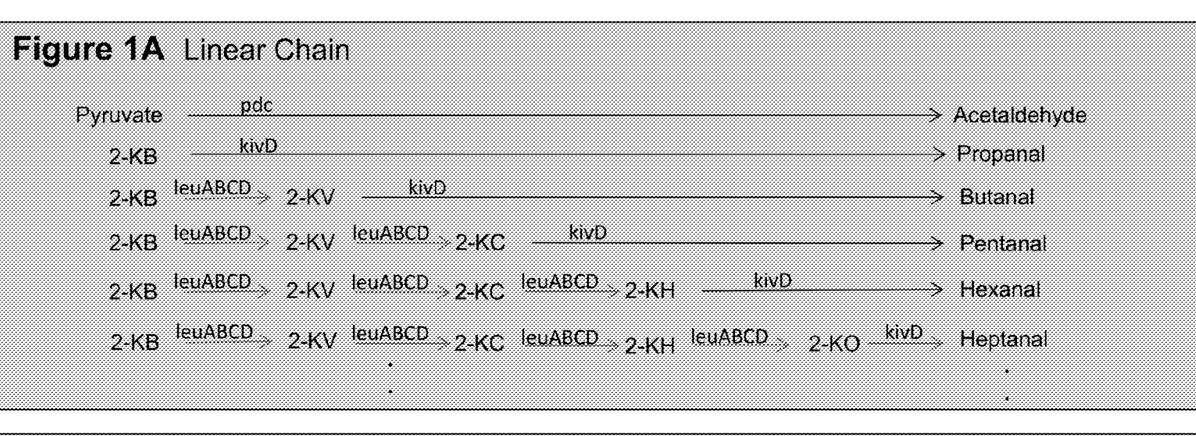
FIG. 1A is an exemplary schematic for metabolic pathways that produce linear chain aldehydes.

FIG. 1A depicts a set of exemplary metabolically engineered pathways for increased production of linear chain aldehydes in a cell. Here, acetaldehyde is formed from pyruvate via the enzyme pyruvate decarboxylase (pdc), and propanal is formed from 2-ketobutyrate (2-KB) via the enzyme 2-ketoisovalerate decarboxylase (kivD). To arrive at longer-chain products, including butanal, pentanal, hexanal, heptanal, etc., metabolically engineered pathways may further include the genes encoding an 2-isopropylmalate synthase (leuA), an 3-isopropylmalate dehydrogenase (leuB), a 3-isopropylmalate isomerase large subunit (leuC), and a 3-isopropylmalate isomerase, small subunit (leuD). Most preferably, these genes are arranged in an operon under appropriate control for expression in a cell. Thus, cells engineered to express leuABCD and kivD will be suitable for production of butanal, pentanal, hexanal, heptanal, etc. from 2-ketobutyrate as depicted through successive chain extension from 2-KB to 2-ketovalerate (2-KV), 2-ketocaproate (2-KC), 2-ketoheptanoate (2-KH), and 2-ketoocanoate (2-KO) and final decarboxylation.

Figure 1B:
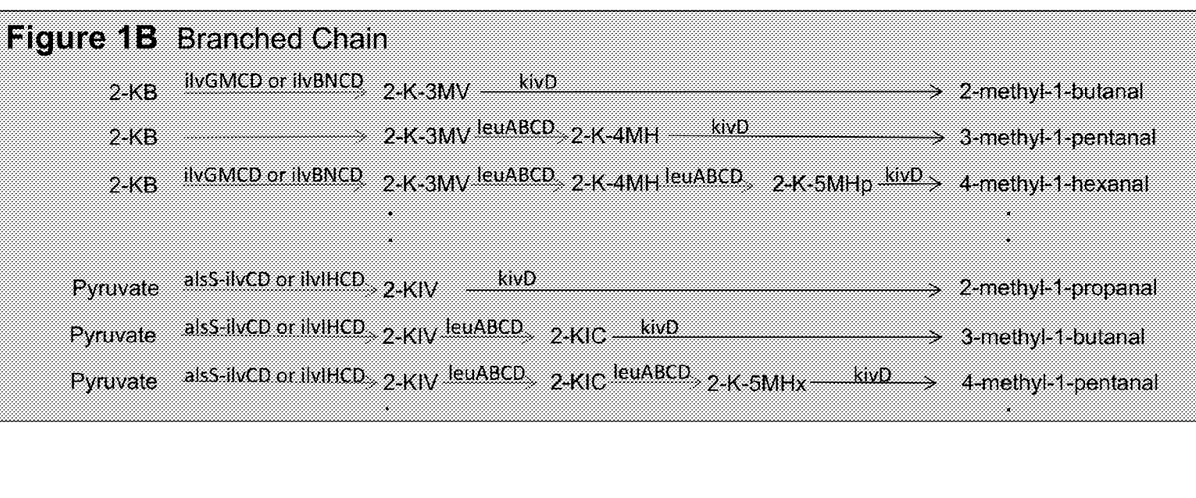
FIG. 1B is an exemplary schematic for metabolic pathways that produce branched chain aldehydes.

FIG. 1B depicts another set of exemplary metabolically engineered pathways for increased production of branched chain aldehydes in a cell. Here, 2-KB is branched to for 2-Ket-3-methylvalerate (2-K-3-MV) via action of gene products of the large subunit of acetohydroxy acid synthase II (ilvG), the small subunit of acetohydroxy acid synthase II (ilvM), acetohydroxy acid isomeroreductase (ilvC), and dihydroxy acid dehydratases (ilvD) or the large subunit of acetohydroxy acid synthase I (ilvB), the small subunit of acetohydroxy acid synthase I (ilvN), acetohydroxy acid isomeroreductase (ilvC), and dihydroxy acid dehydratase (ilvD). 2-K-3-MV may then either the decarboxylated by kivD to form 2-methyl-1-butanal, or may be successively elongated via proteins encoded by leuAB CD to 2-keto-4-methylhexanoate (2-K-4MH) or 2-keto-5-methylheptanoate (2-K-5MHp) prior to decarboxylation by kivD to form respective 3-methyl-1-pentanal and 4-methyl-1-hexanal (and longer branched products). Where the starting material is pyruvate, the pyruvate is first branched by the expression products of the acetolactate synthase (alsS), acetohydroxy acid isomeroreductase (ilvC), and dihydroxy acid dehydratase (ilvD) genes, preferably arranged in a functional expression cassette alsS-ilvCD, or the expression products of the large subunit of acetohydroxy acid synthase III (ilvI), the small subunit of acetohydroxy acid synthase III (ilvH), acetohydroxy acid isomeroreductase (ilvC), and dihydroxy acid dehydratase (ilvD) genes to form 2-ketoisovalerate (2-KIV). Decarboxylation of 2-KIV yields 2-methyl-1-propanal, while chain elongation via expression products of leuABCD yields 2-ketoisocaproate (2-KIC) and 2-keto-5-methylhexanoate (2-K-5Mhx) and higher products. As before, 2-KIC and 2-K-5Mhx are then decarboxylated to the corresponding 3-methyl-1-butanal and 4-methyl-1-pentanal, and higher products.

Therefore, in especially preferred aspects of the inventive subject matter, microbial cells contemplated herein will have increased metabolic activity in branched carbon chain elongation of 2-ketobutyrate to 2-keto-3-methylvalerate via expression of recombinant ilvGMCD genes or expression of recombinant ilvBNCD genes, and/or increased metabolic activity in branched carbon chain elongation of pyruvate to 2-keto-isovalerate via expression of recombinant alsS-ilvCD genes or expression of recombinant ilvIHCD genes.

In still further preferred aspects, contemplated cells will also have an increased metabolic activity in decarboxylation of one or more of 2-ketovalerate, 2-ketocaproate, 2-ketoheptanoate, 2-ketooctanoate, 2-keto-3-methylvalerate, 2-keto-4-methylcaproate, 2-keto-5-methylheptanoate, 2-keto-6-methyloctanoate, 2-keto-isovalerate, 2-ketoisocaproate, 2-keto-5-methylhexanoate, or 2-keto-6-methylocatnoate via expression of a recombinant 2-ketoisovalerate decarboxylase (preferably kivD), and/or an increased metabolic activity in conversion of pyruvate to acetaldehyde via expression of a recombinant pyruvate decarboxylase, and/or an increased metabolic activity in conversion of 2-ketobutyrate to propanal via expression of a recombinant 2-ketoisovalerate decarboxylase. In particularly preferred aspects, cells will further be genetically modified to have an increased metabolic activity in linear carbon chain elongation via expression of recombinant leuABCD genes.

Of course, it should be recognized that all of the genes may be unmodified or may be engineered to impart a desired selectivity, an increased turnover rate, etc. (see e.g., Proc. Nat. Acad. Sci. (2008), 105, no. 52: 20653-20658; WO2009/149240A1). Suitable genes for the activities of the metabolically engineered cells are well known in the art, and use of all of those in conjunction with the teachings presented herein is deemed suitable. Moreover, all of the known manners of making metabolically engineered cells are also deemed suitable for use herein. For example, metabolically engineered cells may modified by genomic insertion of one or more genes, operons, or transfection with plasmids or phagemids as is well known in the art. In some embodiments, a mutant microorganism may also be used in the methods of the present invention, and may be further modified recombinantly as desired.

In further particularly preferred aspects, endogenous alcohol dehydrogenase activity is at least decreased, and more preferably suppressed, and it should be noted that in preferred aspects, all or almost all of the alcohol dehydrogenases will be suppressed or deleted. For example, suppressed or deleted dehydrogenases include adhE, ldhA, frdB, and pflB. It is also noted that dehydrogenase activity can be suppressed or deleted suppressed in numerous well known manners, including down-regulation (e.g., via antisense RNA or siRNA) or disruption of a gene encoding the dehydrogenase, introduction of a knock-down or knock-out mutation, etc.). Consequently, contemplated genetically modified cells will have more than one dehydrogenase mutated or otherwise suppressed.

Viewed from a different perspective, it is therefore contemplated that the genetically modified cells will not produce any significant quantities of short-chain (up to C6, linear or branched) alcohols. For example, such modified cells will release into the fermentation media significantly higher quantities of aldehydes relative to the corresponding alcohols, most typically at a molar ratio of an aldehyde to a corresponding alcohol (e.g., butyraldehyde to butanol) of at least 3:1, more typically at least 4:1, and most typically at least 5:1. Consequently, total short-chain (up to C6, linear or branched) alcohol in the fermentation medium will be less than 1 wt % of the fermentation medium, more typically less than 0.5 wt %, most typically less than 0.1 wt %. Thus, in especially preferred aspects, modified cells will not produce any detectable alcohol (i.e., less than 10 mg/l fermentation medium).

The recombinant microorganism may be any suitable microorganism, including bacteria, cyanobacteria, or a fungus. However, non-photosynthetically active microorganisms are particularly preferred. Therefore, in some embodiments, the microbial cells belong to a genus selected from the group consisting of *Escherichia*, *Bacillus*, *Corynebacterium*, *Ralstonia*, *Zymomonas*, *Clostridium*, *Lactobacillus*, *Synechococcus*, *Synechocystis*, *Saccharomyces*, *Pichia*, *Candida*, *Hansenula*, and *Aspergillus*. In preferred embodiments, the microorganism is consisting *Escherichia coli*, *Bacillus subtilis*, *Synechococcus elongatus*, *Ralstonia eutropha*, and *Saccharomyces cerevisiae*.

It should further be appreciated that the culture conditions will typically depend on the particular choice of microorganism, and the person of ordinary skill in the art will be readily able to chose the appropriate medium. Among other suitable choices, it is generally preferred that the carbon source in the medium is a saccharide, and particularly glucose, fructose, sucrose, starch, cellulose, a hemicellulose, glycerol, carbon dioxide, a protein, and/or an amino acid. However, numerous alternative carbon sources are also deemed suitable, and exemplary further carbon sources include lipids, proteins, CO2, CH4, complex organic mixtures (e.g., biosolids, meat processing waste products, plant based materials, etc.) Regardless of the particular culture condition, the volatile aldehyde is removed from the fermentation medium in the vapor phase. More preferably, such removal will be performed in a continuous fashion during cell culture, and removal may be based on agitation of the fermentation medium, stripping the fermentation medium with an inert gas, stripping the fermentation medium with an oxygen containing gas, and/or temporarily binding the aldehyde to a binding agent. Alternatively, aldehyde removal may also be performed after fermentation, or in a semi-continuous manner (e.g., by intermittent contact with stripping gas).

With respect to further processing, it should be recognized that condensation of the aldehyde may be performed in various manners, preferably using a condenser well known in the art, and that the so condensed aldehyde product may be further purified in one or more steps using conventional manners, or may be directly used in a reduction reaction to produce the corresponding alcohol. There are numerous reduction reactions for aldehydes known in the art, and all of them are deemed suitable for use herein. For example, especially suitable reduction reactions include electrochemical reduction, an enzymatic reduction, and a catalytic reduction with hydrogen.

Therefore, it should be appreciated that a method of producing a metabolically engineered microbial cell for use in an alcohol production process will include genetically modifying the microbial cells to have an increased conversion of pyruvate or 2-ketobutyrate to an aldehyde; genetically modifying the microbial cells to have a decreased alcohol dehydrogenase activity such that the microbial cell is substantially devoid of alcohol production; and testing the modified microbial cells for generation in a fermentation medium of a volatile aldehyde in a quantity sufficient to allow stripping of the volatile aldehyde from the fermentation medium to thereby allow for an ex vivo reduction of the aldehyde to a corresponding alcohol.

Where desired, it is also contemplated that the cells presented herein need not be employed for alcohol production, but for generation of various aldehydes, and especially volatile aldehydes. In such case, the cells are genetically modified as described above and cultivated under conditions suitable for production of the aldehyde. Most typically, the so produced aldehyde is then stripped from the culture medium and condensed for sale, or further use or storage.

Additionally, it should be appreciated that contemplated methods, cells, and processes will also advantageously allow production of desirable compounds other that alcohols where a precursor of the desirable compound is an aldehyde. For example, where the fermentation product of the genetically modified cell is acetaldehyde, especially preferred product that are prepared ex vivo from acetaldehyde are ethanol and acetic acid. Similarly, where the fermentation product of the genetically modified cell is propionaldehyde, especially preferred product that are prepared ex vivo from propionaldehyde include n-propanol, n-propyl acetate, propionic acid, and cellulose acetate propionate. Likewise, where the fermentation product of the genetically modified cell is n-butyraldehyde, especially preferred product that are prepared ex vivo from n-butyraldehyde include n-Butanol, 2-ethylhexanol, poly vinyl butyral, 2-ethylhexanoic acid, methyl amyl ketone, n-butyric acid, n-butyl acetate, n-butyl acrylate, and cellulose acetate butyrate. Where the fermentation product of the genetically modified cell is isobutyraldehyde, especially preferred product that are prepared ex vivo from isobutyraldehyde include isobutanol, isobutyric acid, neopentyl glycol, methyl isoamyl ketone, isobutyl acetate, isobutyl acrylate, 2,2,4-trimethyl-1,3-pentanediol, 2,2,4-trimethyl-1,3-pentanediol, monoisobutyrate, 2,2,4-trimethyl-1,3-pentanediol diisobutyrate, and isobutyl isobutyrate.

Examples

DNA Manipulation: Standard recombinant DNA technologies were used in the examples, which are well known to the skilled man in this field as described in Molecular Cloning: A Laboratory Manual (Cold Spring Harbor Laboratory Press, 1989) by Sambrook J et al.

Gene Knockout: All the genetic knock-outs were achieved with P1 transduction using appropriate Keio collection strains (Construction of *Escherichia coli* K-12 in-frame, single-gene knockout mutants: the Keio collection, Mol. Syst. Biol. 2:2006.0008 (2006)). The Kanamycin resistance gene were eliminated using pCP20 (One-step inactivation of chromosomal genes in *E. coli* using PCR products, Proc. Natl. Acad. Sci., 97: 6640-6645 (2000)) in between each consecutive knockout.

Fermentation: *E. coli* strains were cultured overnight in LB with appropriate antibiotics at 37° C. The next day, the overnight cells were subcultured (usually 1:100) in 250 ml-screw cap flasks containing 10-20 ml of M9 media (64 g Na2HPO4.7H2O, 15 g KH2PO4, 2.5 g NaCl, 5 g NH4Cl, 2 mM MgSO4, 0.1 mM CaCl2, 10 mg thiamine per liter water) with 5 g/liter yeast extract, 40 g/liter glucose, and appropriate antibiotics. The cultures were then incubated at 37° C. in a rotary shaker (250 rpm). To reduce the loss of isobutyraldehyde, the cultures were chilled to 4° C. for 30 min prior to sampling.

GC Analysis: Isobutyraldehyde and isobutanol were quantified by gas chromatography (GC) equipped with a FID (flame ionization detector). The system consisted of a model 7890A GC and model 7693 automatic injector (Agilent Technologies). A 30 m with internal diameter of 0.32 mm, 0.25 µm DB-FFAP capillary columns (Agilent Technologies) was used. GC oven temperature was held at 85° C. for 3 min and raised with a gradient of 45° C./min until 225° C. and held 3 min. Detector and Inlet temperature was held at 225° C. Hydrogen, air and helium gas was used with flow rates of 40 ml/min, 450 ml/min, 45 ml/min, respectively. The supernatant of culture broth was injected in split injection mode (1:25 split ratio) using 1-pentanol as the internal standard.

Construction of the Plasmids for Isobutyraldehyde Production: pEB121: Plasmid pEB0121 was constructed by DNA assembly of four fragments. The first fragment, containing the PLlacO1 promoter, p15A replication origin, and the gene for kanamycin resistance, was amplified with primers 1 and 2 from a derivative of pZE21-MCS1 (Independent and tight regulation of transcriptional units in *Escherichia coli* via the LacR/O, the TetR/O and AraC/I1-I2 regulatory elements. Nucleic Acids Res 25:1203-10 (1997)). In this pZE21-MCS1 derivative, PLtetO1 is replaced with PLlacO1 as a result of a promoter swap with pZE12-luc (Independent and tight regulation of transcriptional units in *Escherichia coli* via the LacR/O, the TetR/O and AraC/I1-I2 regulatory elements. Nucleic Acids Res 25:1203-10 (1997)) using the AatI and Acc65I restriction sites. The second fragment was amplified with primers 3 and 4 from *B. subtilis* genomic DNA as the template. The third fragment contained ilvC, which was amplified with primers 5 and 6 from *E. coli* genomic DNA (ATCC 10789D-5) as the template. The fourth fragment containing ilvD was amplified with primers 7 and 8 with *E. coli* genomic DNA (ATCC 10789D-5) as the template.

```
Primer 1:
5'- ACGCGTGCTAGAGGCATCAAA-3';

Primer 2:
5'-TGTACCTTTCTCCTCTTTAATGAATTCGGTCAGTGCG -3';

Primer 3:
5'-TTAAAGAGGAGAAAGGTACAATGTTGACAAAAGCAACAAAAGAACAA
A -3';

Primer 4:
5'- CATGGTGATTCCTCGTCGACCTAGAGAGCTTTCGTTTTCA -3';

Primer 5:
5'- GTCGACGAGGAATCACCATGGCTAACTACTTCAATAC -3';

Primer 6:
5'-ATGGTATATCTCCTTCCGGGTTAACCCGCAACAGCAATAC -3';
```

-continued

Primer 7:
5'-CCCGGAAGGAGATATACCATGCCTAAGTACCGTTCCGC -3';

Primer 8:
5'-TTGATGCCTCTAGCACGCGTTTAACCCCCCAGTTTCGATT -3'.

pEB5: Plasmid pEB0005 was constructed by DNA assembly of two fragments. The vector was amplified by amplification of pZE12-luc (Independent and tight regulation of transcriptional units in *Escherichia coli* via the LacR/O, the TetR/O and AraC/I1-I2 regulatory elements. Nucleic Acids Res 25:1203-10 (1997)) with primers 9 and 10. The kivd gene was amplified from *Lactococcus lactis* genomic DNA with primers 11 and 12.

Primer 9:
5'- TCTAGAGGCATCAAATAAAACGAAAGG -3';

Primer 10:
5'-GGTACCTTTCTCCTCTTTAATGAATTC -3';

Primer 11:
5'-TTAAAGAGGAGAAAGGTACCATGTATACAGTAGGAGATTA -3';

Primer 12:
5'-TTTTATTTGATGCCTCTAGAATGATTTATTTTGTTCAGCA -3'

Construction of the Isobutyraldehyde Production Host Strain: *E. coli* BW25113 (Datsenko and Warner 2000) was used as wild-type. To eliminate IPTG induction, lacI gene was first knocked out. And then, the major alcohol dehydrogenases are serially knocked out to construct platform strain, EB4 (*E. coli* BW25113ΔlacIΔadhEΔyqhDΔyiaY), for isobutyraldhyde production. Elimination of alcohol dehydrogenases could enhance isobutyraldehyde production by blocking conversion into isobutanol as shown in Table 1 (All strains are harboring two plasmids, pEB5 and pEB121).

TABLE 1

| Strain | Isobutyraldehyde (g/L) | Isobutanol (g/L) |
|---|---|---|
| BW25113 | 1.4 | 5.5 |
| BW25113ΔlacI | 1.5 | 5.5 |
| BW25113ΔlacIΔadhE | 3.5 | 3.0 |
| BW25113ΔlacIΔadhEΔyqhD | 4.5 | 1.2 |
| BW25113ΔlacIΔadhEΔyqhDΔyiaY | 5.0 | 0.5 |

Elimination of Residual Alcohol Dehydrogenase Activity enhanced Isobutyraldehyde Production: Microorganisms have lots of non-specific alcohol dehydrogenase genes. Especially, in *E. coli*, more than 100 alcohol dehydrogenases were found by searching enzyme data bases. Eliminating those non-specific alcohol dehydrogenases from EB4 strain would be beneficial for the isobutyraldehyde production by preventing conversion into isobutanol. In this example, we further eliminated the candidate alcohol dehydrogenase gene, yjgB, to check this hypothesis. As shown in Table 2, further elimination of residual alcohol dehydrogenase activity was beneficial for the isobutyraldehyde production.

TABLE 2

| | Isobutyraldehyde (g/L) | Isobutanol (g/L) |
|---|---|---|
| EB4 (pEB5 + pEB121) | 5.49 | 3.9 |
| EB4ΔyjgB (pEB5 + pEB121) | 6.25 | 2.61 |

Knockout for Competing Metabolic Pathways to enhance Isobutyraldehyde Production: Metabolic pathway for isobutyraldehyde production has several competing pathways for the utilization of key intermediates including pyruvate and 2-ketoisovalerate. By knocking out those competing pathway genes, we could enhance metabolic carbon flow toward our isobutyraldehyde production pathway. To do this, we selected poxB, which convert pyruvate to acetate and ilvE, which convert 2-ketoisovalerate to L-valine. As shown Table 3, it was found to enhance isobutyraldehyde production slightly. However, by combining those competing pathway knockouts, the effect on isobutyraldehyde production was significant as shown in Table 4.

TABLE 3

| | Isobutyraldehyde (g/L) | Isobutanol (g/L) |
|---|---|---|
| EB4 (pEB5 + pEB121) | 5.45 | 1.5 |
| EB4ΔilvE (pEB5 + pEB121) | 5.55 | 1.4 |
| EB4ΔpoxB (pEB5 + pEB121) | 5.77 | 1.5 |

TABLE 4

| | Isobutyraldehyde (g/L) | Isobutanol (g/L) |
|---|---|---|
| EB4 (pEB5 + pEB121) | 7.40 | 1.7 |
| EB4ΔilvEΔpoxB (pEB5 + pEB121) | 8.30 | 2.0 |

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A metabolically engineered microbial cell, comprising:
   a recombinant nucleic acid encoding a pyruvate decarboxylase or a 2-ketoisovalerate decarboxylase;
   a promoter element operably coupled to the recombinant nucleic acid to express the pyruvate decarboxylase or the 2-ketoisovalerate decarboxylase in an amount effective to increase conversion of pyruvate or 2-ketobutyrate to an aldehyde as compared to the same cells without the recombinant nucleic acid;
   a knockout mutation in at least one pathway converting pyruvate to acetate; and
   a mutation or deletion of adhE or yqhD;
   wherein the mutation or deletion decreases alcohol dehydrogenase activity in the metabolically engineered microbial cell such that the alcohol dehydrogenase activity is decreased at least 70% as compared to the same cells without the mutation or deletion.

2. The microbial cell of claim 1 having a further mutation or further deletion of a non-specific alcohol dehydrogenase.

3. The microbial cell of claim 2 wherein the non-specific alcohol dehydrogenase is encoded by yjgB.

4. The microbial cell of claim 1 wherein the decreased alcohol dehydrogenase activity in the microbial cells is decreased at least 90% as compared to the same cells without the mutation or deletion.

5. The microbial cell of claim 1 wherein the recombinant nucleic acid is provided as plasmid or is integrated into the host cell genome.

6. The microbial cell of claim 1 wherein the recombinant nucleic acid encodes a pyruvate decarboxylase.

7. The microbial cell of claim 1 wherein the recombinant nucleic acid encodes a 2-ketoisovalerate decarboxylase.

8. The microbial cell of claim 1 further comprising one or more recombinant nucleic acid for expression of leuA, leuB, leuC, and leuD genes.

9. The microbial cell of claim 1 further comprising one or more recombinant nucleic acid for expression of ilvG, ilvM, ilvC, and ilvD genes or one or more recombinant nucleic acid for expression of ilvB, ilvN, ilvC, and ilvD genes.

10. The microbial cell of claim 1 further comprising one or more recombinant nucleic acid for expression of alsS, ilvC, and ilvD genes or one or more recombinant nucleic acid for expression of ilvI, ilvH, ilvC, and ilvD genes.

11. The microbial cell of claim 1 wherein the microbial cells belong to a genus selected from the group consisting of *Escherichia, Bacillus, Corynebacterium, Ralstonia, Zymomonas, Clostridium, Lactobacillus, Synechococcus, Synechocystis, Saccharomyces, Pichia, Candida, Hansenula*, and *Aspergillus*.

12. The microbial cell of claim 1 wherein the microbial cells belong to a species selected from the group consisting *Escherichia coli, Bacillus subtilis, Synechococcus elongatus, Ralstonia eutropha*, and *Saccharomyces cerevisiae*.

13. The microbial cell of claim 1 wherein the cell is disposed in a medium having a carbon source selected from the group consisting of glucose, fructose, sucrose, starch, cellulose, a hemicellulose, glycerol, carbon dioxide, a protein, and an amino acid.

14. A fermentation medium containing the microbial cell of claim 1, wherein the cell produces more isobutyraldehyde (g/L) than isobutanol (g/L).

15. The fermentation medium of claim 14 containing isobutyraldehyde at a concentration of between 0.5 g/L and 4.0 g/L.

16. The fermentation medium of claim 14 having a carbon source selected from the group consisting of glucose, fructose, sucrose, starch, cellulose, a hemicellulose, glycerol, carbon dioxide, a protein, and an amino acid.

17. The fermentation medium of claim 14 comprising undissolved gas in an amount effective to displace isobutyraldehyde into a vapor phase above the medium.

18. A method of producing an alcohol, comprising:
growing a plurality of microbial cells in a fermentation medium, wherein the cells are genetically modified to have an increased metabolic activity as compared to the same cells without modification;
wherein the increased metabolic activity is characterized by increased conversion of pyruvate or 2-ketobutyrate to an aldehyde via introduction and expression of recombinant pyruvate decarboxylase or 2-ketoisovalerate decarboxylase, respectively, and via a knockout mutation in a pathway converting pyruvate to acetate;
wherein the plurality of microbial cells are further genetically modified to have a decreased alcohol dehydrogenase activity, wherein the alcohol dehydrogenase activity is decreased at least 70% as compared to the same cells without further modification, and wherein the decreased alcohol dehydrogenase activity is due to deletion of adhE and yqhD, and optionally deletion of a non-specific alcohol dehydrogenase;
continuously or semi-continuously removing the aldehyde in a vapor phase from the fermentation medium;
condensing the aldehyde from the vapor phase; and
reducing the condensed aldehyde to the corresponding alcohol.

19. The method of claim 18 wherein the microbial cells have increased metabolic activity in decarboxylation of one or more of 2-ketovalerate, 2-ketocaproate, 2-ketoheptanoate, 2-ketooctanoate, 2-keto-3-methylvalerate, 2-keto-4-methylcaproate, 2-keto-5-methylheptanoate, 2-keto-6-methyloctanoate, 2-keto-isovalerate, 2-ketoisocaproate, or 2-keto-5-methylhexanoate via expression of a recombinant 2-ketoisovalerate decarboxylase.

20. The method of claim 18 wherein the microbial cells have increased metabolic activity in branched carbon chain elongation of 2-ketobutyrate to 2-keto-3-methylvalerate via expression of one or more recombinant nucleic acids encoding ilvG, ilvM, ilvC, and ilvD genes or via expression of one or more recombinant nucleic acid encoding ilvB, ilvN, ilvC, and ilvD genes.

21. The method of claim 18 wherein the microbial cells have increased metabolic activity in branched carbon chain elongation of pyruvate to 2-keto-isovalerate via expression of one or more recombinant nucleic acid encoding alsS, ilvC, and ilvD genes or via one or more recombinant nucleic acid encoding ilvI, ilvH, ilvC, and ilvD genes.

22. The method of any one of claim 19, claim 20, or claim 21, wherein the microbial cells have increased metabolic activity in linear carbon chain elongation via expression of one or more recombinant nucleic acid encoding leuA, leuB, leuC, and leuD genes.

23. The method of claim 18 wherein the microbial cells belong to a genus selected from the group consisting of *Escherichia, Bacillus, Corynebacterium, Ralstonia, Zymomonas, Clostridium, Lactobacillus, Synechococcus, Synechocystis, Saccharomyces, Pichia, Candida, Hansenula*, and *Aspergillus*.

24. The method of claim 23 wherein the microbial cells belong to a species selected from the group consisting *Escherichia coli, Bacillus subtilis, Synechococcus elongatus, Ralstonia eutropha*, and *Saccharomyces cerevisiae*.

25. The method of claim 18 wherein the fermentation medium has a carbon source selected from the group consisting of glucose, fructose, sucrose, starch, cellulose, a hemicellulose, glycerol, carbon dioxide, a protein, and an amino acid.

* * * * *